(12) United States Patent
Brandimarte

(10) Patent No.: US 12,053,577 B2
(45) Date of Patent: Aug. 6, 2024

(54) SYSTEM FOR THE MOLECULAR VAPORIZATION OF A LIQUID SUBSTANCE

(71) Applicant: NUTRINTECH MED ITALIA S.R.L., Rome (IT)

(72) Inventor: Bruno Brandimarte, Nettuno (IT)

(73) Assignee: NUTRINTECH MED ITALIS S.R.L., Rome (IT)

( * ) Notice: Subject to any disclaimer, the term of this patent is extended or adjusted under 35 U.S.C. 154(b) by 901 days.

(21) Appl. No.: 17/253,499

(22) PCT Filed: Jun. 17, 2019

(86) PCT No.: PCT/IB2019/055027
§ 371 (c)(1),
(2) Date: Dec. 17, 2020

(87) PCT Pub. No.: WO2019/243987
PCT Pub. Date: Dec. 26, 2019

(65) Prior Publication Data
US 2021/0252232 A1   Aug. 19, 2021

(30) Foreign Application Priority Data

Jun. 18, 2018 (IT) .......................... 102018000000391

(51) Int. Cl.
*A61M 15/06* (2006.01)
*A61M 11/00* (2006.01)
(Continued)

(52) U.S. Cl.
CPC .......... *A61M 15/06* (2013.01); *A61M 11/005* (2013.01); *A61M 11/042* (2014.02); *A61M 15/0085* (2013.01); *A61M 15/0086* (2013.01)

(58) Field of Classification Search
CPC ................ A61M 11/041; A61M 15/08; A61M 15/0003; A61M 15/001; A61M 15/06;
(Continued)

(56) References Cited

U.S. PATENT DOCUMENTS 6,196,219 B1   3/2001   Hess et al.
8,714,150 B2   5/2014   Alelov
(Continued)

FOREIGN PATENT DOCUMENTS

EP           1916009 A1 *  4/2008  .......... A61M 11/048
WO   WO-2008077271 A1   7/2008
(Continued)

OTHER PUBLICATIONS

Translation of EP 1916009 (Year: 2008).*
(Continued)

*Primary Examiner* — Victoria Murphy
(74) *Attorney, Agent, or Firm* — Sterne, Kessler, Goldstein & Fox P.L.L.C.

(57) ABSTRACT

A system (1) is configured to deliver a liquid substance in the form of dry steam in the context of respiratory therapy. The system (1) comprises: —a reservoir (2) for containing the substance; —dispensing means (6) of the substance in fluid connection with said reservoir (2); —first vibration type electromechanical vaporization means (3), configured to apply vibrations to the substance contained within said reservoir (2) in such a way as to bring the substance into a dry steam state; —second heating vaporization means (4) configured to release thermal energy to the substance contained in said reservoir (2), in such a way as to bring the substance into a dry steam state; —a control unit (7) configured to control the actuation of said first mechanical vaporization means (3) and/or said second heating vaporization means (4) according to a predetermined delivery program.

12 Claims, 4 Drawing Sheets

(51) Int. Cl.
*A61M 11/04* (2006.01)
*A61M 15/00* (2006.01)

(58) Field of Classification Search
CPC .............. A61M 11/005; A61M 11/042; A61M 15/0085; A61M 15/0086
See application file for complete search history.

(56) References Cited

U.S. PATENT DOCUMENTS

| | | |
|---|---|---|
| 2012/0118301 A1 | 5/2012 | Montaser |
| 2012/0227752 A1* | 9/2012 | Alelov .............. A61M 15/0066 131/273 |
| 2017/0181475 A1 | 6/2017 | Camberon et al. |
| 2017/0231278 A1 | 8/2017 | Mironov et al. |
| 2017/0245550 A1 | 8/2017 | Freelander |
| 2017/0367402 A1 | 12/2017 | Lau et al. |

FOREIGN PATENT DOCUMENTS

| | | |
|---|---|---|
| WO | WO-2011065754 A2 | 6/2011 |
| WO | WO-2019243987 A1 | 12/2019 |

OTHER PUBLICATIONS

International Search Report and Written Opinion for International Application No. PCT/IB2019/055027, European Patent Office, Netherlands, mailed on Sep. 20, 2019, 13 pages.

\* cited by examiner

SYSTEM FOR THE MOLECULAR VAPORIZATION OF A LIQUID SUBSTANCE

TECHNICAL FIELD OF THE INVENTION

The present invention refers to a system for the delivery of a liquid substance, configured to carry out the vaporization thereof in the form of saturated dry steam.

The system of the present invention is intended in particular for medical applications, for the purpose of administering a vaporized solution to a patient, containing an active ingredient, which has a high penetration capacity at the level of the lung membrane.

BACKGROUND

The administration in the form of steam of liquid substances comprising medicinal active ingredients is traditionally used in therapies aimed at resolving upper and lower respiratory tract disorders. Such substances generally comprise a medicinal active ingredient bound to a solvent.

Numerous devices are known in the art, such as inhalers, aerosols and nebulizers, suitable for the breakdown of such liquid substances into drops of such size as to be dispersed in the air to allow their delivery to the airways or nasal pharyngeal cavities, bronchial of the patient.

At present, there are basically two methods for projecting substances containing active ingredients into the patient's airway/cavity, in the form of steam or nebulization.

A first method is implemented by means of aerosol or mechanical/electromechanical nebulizer systems. These systems provide the passage of an air flow by a spout, which spout is connected by a small tube to a reservoir containing the solution to be administered. Due to the flow of air, drops of the substance are forced to pass through the tube until they come out of the spout. In such systems, the size and number of drops delivered depends on the speed of the air flow, and is neither adjustable, nor measurable.

A second method provides instead the heating of the solution to be administered by air up to the steam temperature, to allow the inhalation of the steam by the patient.

These delivery methods make it complex to succeed to control the parameters of the substance delivered, in terms of the size of the drops delivered, dosage, pressures, speed and delivery temperature. Therefore, they do not allow the administration therapy to be implemented in a precise and customizable manner, nor to reiterate it in a consistent manner.

Furthermore, the drops obtained by the vaporization operated by devices of the known type, although of reduced size, have a penetration capacity which stops at the level of the patient's bronchi.

U.S. Pat. No. 6,196,219B1 describes an inhaler for the delivery to a patient of a liquid medicinal substance in the form of a dispersion of atomized drops. The inhaler comprises a housing which bears a provision of the liquid to be delivered connected to a spray device, which device can itself make a provision of liquid.

U.S. Pat. No. 8,714,150B2 describes an electronic cigarette for the delivery of one or more substances in the form of gas or steam. The electronic cigarette comprises a housing, a first cartridge, a second cartridge, a power source or battery, a controller and a communication device.

US2012/118301 describes an electronic cigarette comprising a flat transducer for spraying a substance intended to be inhaled by a user. The electronic cigarette comprises a housing within which a reservoir is contained that collects the liquid to be sprayed, and supply means such as a rechargeable battery.

US2017/0245550 describes a vaporizer device that includes means for automatically replacing (or feeding) a liquid substance to be vaporized, when the vaporized dose has been totally inhaled by a user.

US2017/0367402 describes a portable vaporizer device comprising a provision of liquid to be vaporized, a channel connected to said provision, within which said liquid can flow, and a heating element. This element is configured to generate heat to be transferred to the liquid flowing inside the channel in order to vaporize it; for this purpose, the heating element can be limited to the channel, like a coil.

US2017/0181475 describes an electronic cigarette which comprises a control microprocessor, a user data memory device and operating parameters of the device itself and means of access to the Internet network or for connection to further devices.

SUMMARY OF THE INVENTION

The technical problem posed and solved by the present invention is therefore that of providing a system which allows to overcome the drawbacks mentioned above with reference to the prior art.

The aforementioned drawbacks are solved by an independent system according to claim 1.

Preferred features of the present invention are the subject of the dependent claims.

The present invention provides an improved system of vaporization of a liquid substance containing an active ingredient, which allows the substance to be delivered to the patient in the form of saturated dry steam (more briefly also following as dry steam), i.e. decomposed at the molecular level. In fact, as it is known, saturated dry steam represents a particular level state of a liquid substance in which the whole substance is in the form of steam, and any drop of liquid is present.

In fact, the system of the invention is configured to break the molecular bonds of the substance, in particular between the molecules of the active ingredient and the solvent and between the molecules of the active ingredient itself, in order to obtain free molecules.

Advantageously, the substance reduced to molecular dimensions is able to reach not only the bronchi, but also the membrane of the pulmonary alveoli, allowing an effective administration of the active ingredient to the patient.

The system of the invention is configured to process the substance until it reaches the state of saturated dry steam using two modes, which can be implemented independently from each other, alternatively, in series, or simultaneously.

A first method provides the substance to be applied with vibrations at frequencies above a predetermined threshold value, which is a function of the characteristics of the substance itself. The vibrations must have an energy content such as to allow the breakage of the molecular bonds of the substance to obtain dry steam.

A second method provides the transfer of thermal energy to the substance until it reaches a temperature of dry steam, which is a function of the characteristics of the substance itself, such as to break the molecular bonds.

For this purpose, the system comprises mechanical or electromechanical means, which provides the application of vibratory energy, and thermal means, which provides the heating of the substance. According to preferred variants of the proposed system, the mechanical or electromechanical means comprises a ceramic element, in particular suitable for vibrating at an ultrasonic frequency. According to further preferred variants, the mechanical means are configured to emit vibrations at an ultrasonic frequency which can be higher than 5 MHz, or in particular between 4.5 and 5.5 MHz, and/or to generate an energy density greater than 10 $W/cm^2$, preferably between 10-13 $W/cm^2$.

As regards the thermal means, according to preferred embodiments of the invention this is configured to raise the temperature of the substance at least up to 250° C. Indeed, with reference to generic medical solutions, when the 100° C. is reached the temperature of the solution does not increase, but the additional energy supplied causes the breakage of the bonds between the molecules of the solvent and that of the solute.

In accordance with preferred embodiments, the heating of the substance may occur by means of induction means supplied with current at a frequency comprised between 15 and 25 KHz.

Both methods of breaking the molecular bonds of the substance are implemented in a controlled and predeterminable manner thanks to the presence of a control unit, which is connected to the vibratory means and to the heating means.

Advantageously, the preferred operating ranges reported above with reference to the mechanical means and to the thermal means allow to obtain the vaporization of a liquid substance in the form of saturated dry steam in a time shorter than 10 seconds.

According to preferred variants of the invention, the control unit is implemented by means of an electronic microprocessor, configured to control the actuation of the mechanical or electromechanical means and of the thermal means according to a predetermined delivery program based on the specific substance to be delivered and to the prescribed therapy.

This delivery program defines parameters such as for example the frequency of the vibrations to be applied to the substance, the temperature, the pressure and the speed at which the vaporized substance is delivered, the dose of substance to be delivered and the direction in which the steam is released, which is function of the body district target of delivery (e.g. nasal cavities, upper airways, lungs etc.).

Advantageously, in order to allow realizing the delivery of substances according to different programs, in such a way as to use the system in different types of therapies, preferred embodiments of the system comprise an interface configured to allow a user to select different predetermined delivery programs. Alternatively, it is provided the option of manually selecting the delivery parameters, i.e. at least the activation parameters of the mechanical or electromechanical and thermal vaporization means.

Furthermore, particularly advantageous variants of the invention provide the option of simply selecting the substance type to be delivered by means of suitable interface means. Based on the selection made, the control unit activates the mechanical or electromechanical means and/or the thermal means according to predetermined parameters, i.e. according to a predetermined delivery program.

According to further variants, the control unit is configured to be in data communication with a memory unit, where predetermined delivery programs are stored, as well as the associations between these delivery programs and the types of substance that can be selected by means of the interface means.

Furthermore, according to preferred embodiments it is also possible to adjust the delivery mode, choosing between continuous or pulsed delivery, and in the latter case it is possible to program the duration of the pulse, the interval between subsequent pulses, the dosage of delivered substance for each pulse and the total number of delivery pulses.

According to a further particularly advantageous variant, in the system of the invention further means are provided for the connection to an aspirator/compressor (preferably a turbine), in such a way as to be able to also implement a delivery mode of the substance by nebulization thereof.

Such a delivery mode is required for the administration by inhalation (bronchi/lungs) of active ingredients insoluble and/or inserted in liposomes (for example salts, such as the ferric pyrophosphate inserted in liposomes).

Advantageously, the system according to the invention allows to obtain particles of the substance to be delivered, containing a determined active ingredient, with a diameter less than 1 micron, suitable for interstitial delivery. Particularly, particles of such dimensions are suitable to reach the small bronchi and proceed up to the pulmonary alveoli to activate the process of passage in the blood flow of the active ingredient.

Other advantages, features and methods of use of the present invention will become apparent from the following detailed description of some embodiments, presented by way of non-limiting example.

SHORT DESCRIPTION OF THE DRAWINGS

Reference will be made to the attached Figures, in which.

The drawings above indicated are intended exclusively for illustrative and non-limiting purposes.

DETAILED DESCRIPTION OF PREFERRED EMBODIMENTS

Figure 1:
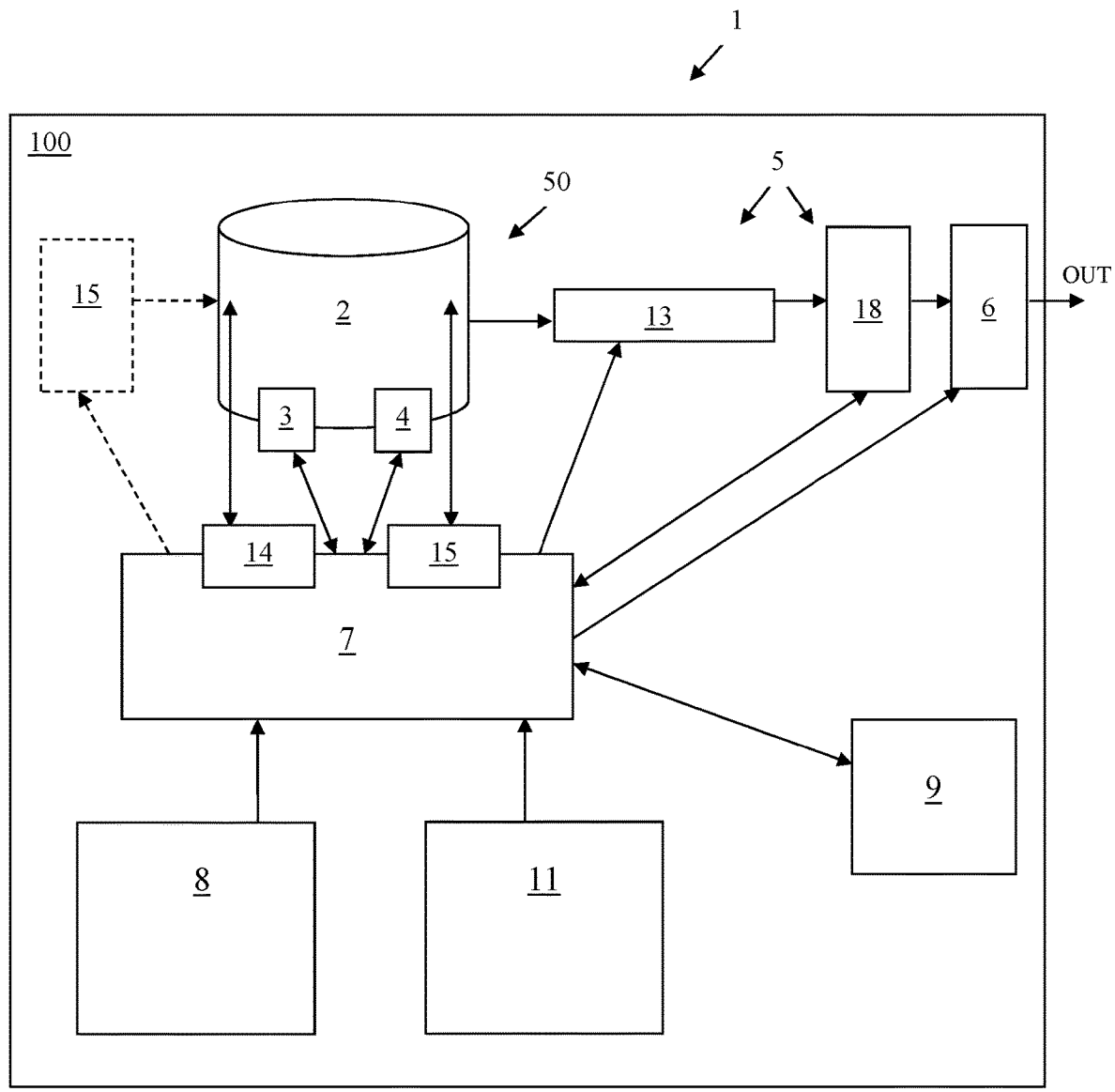
FIG. 1 shows an exemplary block diagram of a first preferred embodiment of a system according to the present invention.

With initially reference to FIG. 1, a preferred embodiment of a system according to the present invention is overall denoted by 1.

The system 1 is configured for the delivery of a liquid substance, comprising a medicinal active ingredient, decomposed at the molecular level in the form of dry steam, to perform a respiratory therapy.

The system 1 preferably has a modular configuration, to allow the implementation of delivery methods which vary depending on the type of substance and respiratory therapy.

The system 1 first of all comprises a support body 100 and a reservoir 2, removably connectable to the latter. The reservoir 2 is configured to contain the liquid substance, and is preferably made of metallic material, or in any case of material compatible with the substance itself.

The reservoir 2 may have a finished screw cap at a section of inlet for the liquid to be vaporized, and has a capacity preferably from 5 to 40 $cm^3$, preferably equal to 15 $cm^3$.

Moreover, the reservoir 2 preferably comprises facilitated access means inside thereof, in such a way as to be easily inspected to allow a periodic cleaning.

The reservoir 2 is in communication with pickup means 5 of the substance, preferably comprising a pump 18 and/or a non-return valve 13, configured to prevent the steam from being repelled into the reservoir 2 by the pump 18. The pump 18 is configured in particular to withdraw and expel steam in quantitatively predefined doses, and at a pressure programmable by a control unit 7, which will be discussed below. These pickup means 5 is removably connectable to the reservoir 2.

Furthermore, sensors or probes 14, 15 may be housed within the reservoir 2, configured respectively for the detection of pressure and temperature of the substance, so that such parameters can be monitored during its vaporization within the reservoir 2. In particular, heating above 100° C. may bring the pressure inside the reservoir to about 3 atmospheres; in general, for substances in solution, this pressure promotes the solute molecules to release from those of solvent.

The probes 14, 15 are in communication with the control unit 7. Furthermore, means for regulating the pressure and temperature of the substance present in the reservoir 2, connected to the control unit 7, can be present.

The system 1 further comprises dispensing means 6 of the substance, placed in fluid connection with the pickup means 5. This means 6 comprises for example one or more nasal and/or oral delivery devices, such as masks or tubes provided with nozzles of various shapes and lengths depending on the delivery target, which can be mouth, nose, ear or other cavity or surface to be treated.

The dispensing means 6 is shaped to allow the delivery of the substance according to predetermined direction and speed parameters, which depend exactly on the area and the geometry of the passage section of the substance to be delivered. Therefore, it is advantageously foreseeable that this dispensing means 6 is selectively interchangeable, in order to be able to select them according to the specific application required.

The dispensing means 6 is preferably equipped with a block valve, which normally allows the passage of the steam, and which can be closed to stop the delivery by command of the control unit 7. The control unit 7 controls the closure of the block valve when a predefined dose of substance is delivered; in this way, the dosage control of the substance delivered to the patient is operated.

The system 1 also comprises mechanical or electromechanical first vaporization means 3, of the vibration type, configured to apply vibrations to the substance contained in the reservoir 2 in such a way as to bring it into a dry steam state.

The first vaporization means 3 is preferably configured to apply ultrasonic frequency vibrations to the substance, in particular at a frequency of at least 3 MHz, preferably greater than or equal to 5 MHz. Furthermore, first vaporization means 3 can be configured to generate in association with such vibrations an energy density sufficient to break the molecular bonds of the substance, for example at least equal to 3 W/cm$^2$, preferably equal to or greater than 10 W/cm$^2$.

Even more preferably, the first vaporization means 3 is configured to emit vibrations at an ultrasonic frequency between 4.5 and 5.5 MHz, and/or to generate an energy density preferably between 10-13 W/cm$^2$. In association with this energy density, a release of saturated dry steam is obtained at a pressure of 1,000 millibars.

In other words, the first vaporization means 3 is configured to apply mechanical vibratory energy, with adjustable frequency and energy density, which allows the substance to reach the molecular dimension by breaking the bonds between the molecules, bringing it into the dry steam state. In particular, the first vaporization means 3 comprises a vibrating element made of ceramic material.

Furthermore, the system 1 comprises second vaporization means 4 of the heating type, configured to transfer thermal energy to the substance contained in the reservoir 2, in such a way as to break the molecular bonds and bring it into the dry steam state.

The second vaporization means 4 is configured to bring the temperature of the substance to the saturated dry steam temperature, for example to at least 250° C. for a substance with a boiling temperature at 100° C.

Preferably, the second vaporization means 4 is configured to be supplied with current at a frequency of between 15 and 25 KHz.

According to preferred embodiments of the invention, the second vaporization means 4 comprises induction heating elements, preferably applied at least at a bottom portion of the reservoir 2. In particular, the second vaporization means 4 can be implemented so as to allow, if desired, hot vaporization, or to heat the steam produced by execution of the first vaporization means 3.

In particular, the first vaporization means 3 is configured to apply vibrations at ultrasonic frequencies comprised between 4.5 and 5.5 MHz to the liquid substance, generating an energy density between 10-13 W/cm$^2$, and the second vaporization means 4 comprises induction means supplied with current frequency between 15 and 25 KHz, configured to bring the temperature of the substance to at least 250° C., the configuration of the system 1 being such as to carry out the vaporization of the liquid substance in the form of saturated dry steam in a time less than 1 second.

Basically, both of such vaporization means having a mechanical or electromechanical action 3 and thermal action 4 are configured to produce an increase in the energy content of the substance sufficient to break its molecular bonds, bringing it into the physical state of saturated dry steam. Therefore, the vaporization of the substance can be achieved by using only one of these first and second means 3, 4, which can be implemented independently from each other.

Alternatively, the system 1 provides that the vaporization is realized by the simultaneous use of both said first and second means 3, 4, suitably regulated by the control unit 7 or by means of a manual control. For this purpose, the system 1 can comprise interface means 8 connected to the other control unit 7, configured to allow a user to adjust the parameters for the implementation of the first and second vaporization means 3, 4, as well as to select a predetermined delivery program.

This mode of simultaneous actuation is required for example for the treatment of oily substances, the vaporization of which requires the application of vibrations at a frequency greater than or equal to 5 MHz, with energy density up to over 10 W/cm$^2$. Furthermore, it is required to resort to a sharp increase in temperature, which must be higher than the boiling value of the oily substance (e.g. over 200° C.).

As anticipated, the control unit 7, which can be implemented by means of an electronic microprocessor, is configured to command the implementation of the first vaporization means 3 and/or second vaporization means 4 according to parameters that can be defined in a predetermined delivery program, or alternatively they can be manually selected by an operator using interface means 8.

The predetermined delivery program defines at least frequency, duration and energy density values of the vibrations applied by the first vaporization means 3 and/or temperature values and duration of the heating operated by the second vaporization means 4, in association with a specific type of therapy and substance to be delivered. The aforementioned parameters strongly depend on the physical/chemical characteristics of the substance (in particular on the molecular binding energy), which must be brought to more or less high temperatures to reach the dry steam state, or energized at more or less high frequencies.

Moreover, the system 1 may comprise a memory unit 9 connected to or integrated in the control unit 7, wherein predetermined delivery programs are stored, associated with respective types of administration therapy and of substance to be delivered. In this way, it is possible to guarantee the replicability of the therapy for administrating the substance for an indeterminate number of times. In particular, the memory unit 9 can also be realized in the form of a USB key which can advantageously be connectable to the system 1 and to additional external electronic devices, to allow the modification or updating of the predetermined delivery programs.

The control unit 7 can further be configured to regulate the pressure and the temperature of the liquid substance to be vaporized contained in the reservoir 2. As regards the temperature, this is preferably kept comprised between 18° C. and 250° C. Furthermore, the control unit 7 can regulate the quantity of steam delivered and its pressure through the pump 18, the valve 13 and the block valve of the dispensing means 6.

Furthermore, according to particularly advantageous embodiments of the present invention, the first vaporization means 3 and/or the second vaporization means 4 is removably connectable to the support body 100, so as to realize a modular type system.

In particular, the first vaporization means 3 and/or the second vaporization means 4 is integral with the reservoir 2, to achieve a selectively removable vaporiser group 50 from the support body 100.

As a matter of fact, the modularity of the system 1 allows the vaporizer group 50 to be removed from the support body 100, comprising the first vaporization means 3, the second vaporization means 4 and the reservoir 2, to replace them with a further reservoir 2 connected to means of atomizing the substance contained in it. In this way, the system 1 allows to realize also a delivery mode for nebulization, in addition to the one that foresees the generation of dry steam.

The spraying means comprises a compressor 15, preferably provided with a filter, shown with a dotted line as an example in FIG. 1, and connection means configured to realize a fluid communication between the reservoir 2 and the compressor 15. The reservoir 2, the compressor 15 and their respective connection means realize a nebulizer group, denoted by the numerical reference 60 in FIG. 2.

Figure 2:
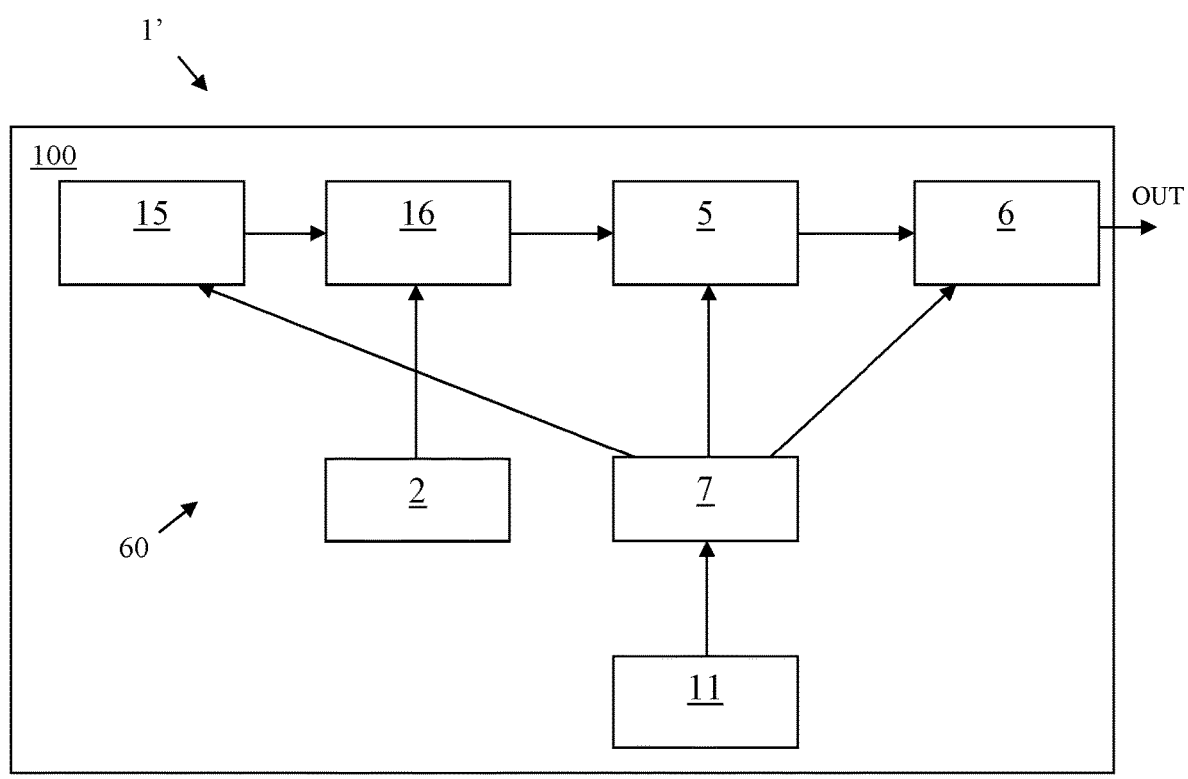
FIG. 2 shows an exemplary block diagram of a second preferred embodiment of a system according to the present invention.

With yet reference to FIG. 2, a further form of realization of the system 1' of the invention is shown, of which only some of the components which will be described below are represented. The components not represented in FIG. 2, as well as those not covered by the following description of the system 1', are considered equal to those comprised in the system 1.

The system 1' comprises, instead of the vaporizer group 50 consisting of the first vaporization means 3, the second vaporization means 4 and the reservoir 2, a nebulizer group 60, comprising the anti-reservoir 2 for containing a further substance, the compressor 15 and connection means 16, the latter configured to realize a fluid communication between the further reservoir 2 and the compressor 15. The connection means 16 has a beak conformation, such as to regulate in a predetermined manner the size of the droplets that constitute the flow of nebulized substance to be delivered.

Both the further reservoir 2 and the compressor 15, which are preferably integral with each other, are removably connected to the support body 100. The compressor 15 is also removably connected to the control unit 7, while the further reservoir 2 is removably connected to the pickup means 5.

In particular, the compressor 15 can work at a pressure between 0.5 and 3.5 (preferably equal to 1.5) atmospheres, while the pickup means 5 can comprise a dispensing pump which operates at a pressure of between 0.5 and 3.5 (preferably equal to 2.5) atmospheres.

According to such variant, the configuration of the system 1' is such as to allow the nebulization and delivery of the further substance contained in the reservoir 2 by actuation of the compressor 15 by the control unit 7, according to a predetermined delivery program or a manual selection of the operating parameters of the compressor 15. This variant 1' is intended for delivering non-vaporizable substances, thus increasing the versatility of the invention.

As anticipated, by means of the appropriate configuration of the means 16, it is possible to adjust the size of the nebulized droplets, which can be for example between 2 and 20 microns.

The power supply of the system 1, 1' can be left to a rechargeable battery 11, connected to the control unit 7. Advantageously, the operation of the system 1, 1' can be provided during the battery charging phase 11.

In the light of what has been so far described, the system 1, 1' according to the present invention can be advantageously used for the delivery of aqueous solutions, or aqueous suspensions in the case of vaporizable insoluble active ingredients at high steam temperature, as well as for delivering non-aqueous solutions, vaporizable at room temperature, or solutions with the necessity of vaporization at intermediate temperature. For example, the invention makes it possible to supply thermal waters, including ferrous waters, to reproduce the thermal conditions at home.

Furthermore, the configuration of the system 1' which provides the compressor 15, allows to realize the nebulization of adhesive mucus substances. Furthermore, the nebulization allows to deliver insoluble active ingredients, even if inserted into liposomes. In this way, the active ingredient can be taken by inhalation (bronchi/lungs) even if it is insoluble and/or inserted into liposomes (for example salts, such as ferric pyrophosphate). Advantageously, the invention allows drops of adhesive mucus substances to be projected directly into the throat at room temperature, which drops will form a protective film when they come into contact with the throat, due to the temperature of the mucosa.

Advantageously, the invention enables a substance to be delivered, in which parameters such as the dose (quantity of product) delivered, the pressure, the projection speed and, in the case of the nebulization variant, also the diameter of the nano-drops constituent nebulizes mist are electronically controlled. These parameters can be stored in the memory unit 9, in association with each predetermined delivery program.

Moreover, by virtue of the modularity of the system 1, 1' and the interchangeability among the vaporiser group 50 and the nebulizer group 60, it is possible to select different delivery modes, for example it can be chosen among molecular steam at room temperature, heated molecular steam at programmed temperature or nebulization with predetermined droplet size.

Furthermore, the invention may provide that the control unit 7 controls a delivery of the substance, both in vaporization and nebulization conditions, according to a continuous mode or according to a pulsed mode, according to a predetermined delivery program or to a manual type selection. In the case of pulsed delivery, the pulse duration, the interval between one pulse and the next, the dosage of substance delivered for each pulse, as well as the total number of pulses, can be programmed.

Reference will now be made to the attached FIG. 3, in which the block diagram of a third preferred embodiment of a system according to the present invention, denoted with 1000, is shown. In addition to the components shown in FIG. 3, the system 1000 can comprise further components comprised in system 1 and/or 1'. All the components comprised within the system 1000 and not represented in FIG. 3, as well as those not covered by the following description of the system 1000, are understood to be equal to those comprised within system 1. The system 1000 comprises a reservoir 22 which has a 'double chamber'. As shown in detail in FIG. 4, in particular the reservoir 22 comprises a first chamber 25 and a second chamber 26. The second chamber 26 is preferably configured in such a way as to circumscribe, at least partially, the first chamber 25. According to this preferred configuration, the first chamber 25 is at least partially contained within the second chamber 26.

The first chamber 25 is furthermore in fluid connection with the second chamber 26, in particular the first chamber 25 can have an inlet opening at one of its bottom walls—or not have any bottom wall at all—this opening facing inside the second chamber 26, in particular on a bottom wall 39 of the aforementioned second chamber 26.

The system 1000 further comprises, in association with the aforementioned reservoir 22, first and second vaporization means 3, 4. In particular, the system 1000 has heating means comprising an inductor 29, connected to a respective induction generator 35, and vibratory means preferably comprising a ceramic element 33, adapted to vibrate at ultrasonic frequencies, connected to a respective ultrasound generator 34.

Figure 4:
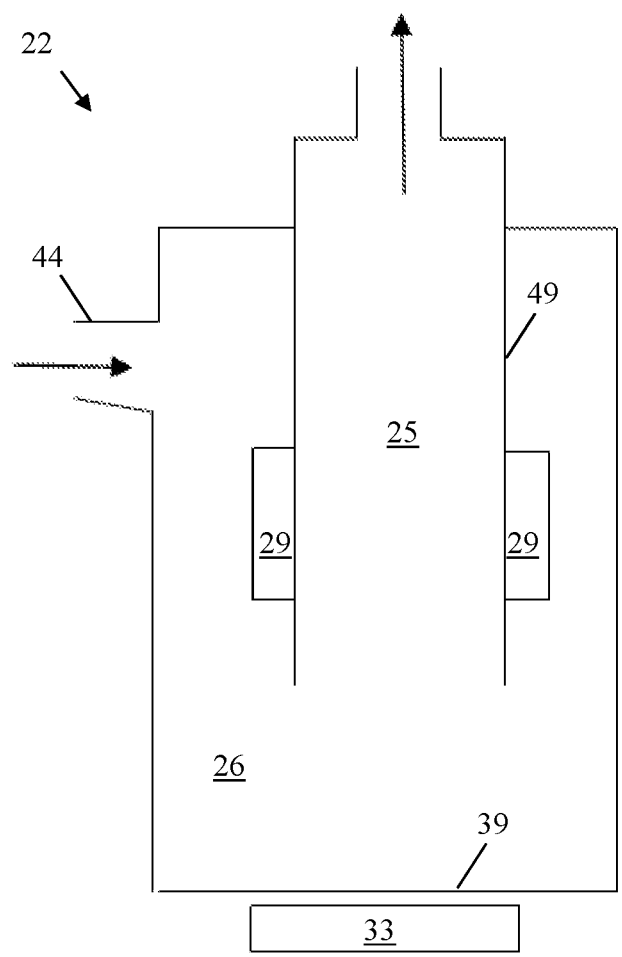
FIG. 4 shows in detail, schematically, a preferred embodiment of a reservoir comprised in a system according to the embodiment shown in FIG. 3.

According to the preferred embodiment shown in FIG. 4, the ceramic element 33 apt to vibrate at ultrasonic frequencies is associated with the aforementioned bottom wall 39 of the second chamber 26, preferably outside said chamber 26. The inductor 29 is instead preferably associated with the first chamber 25, in particular at a side wall 49, preferably outside the first chamber 25.

The induction generator 35 and the ultrasound generator 34 are selectively activated to allow the vaporization of the substance to be delivered to the patient.

Preferably, the substance to be vaporized is contained within the second chamber 26 and is brought to the state of saturated dry steam by the action of the ultrasonic frequency vibrating means. The steam thus obtained flows to the first chamber 25 and is therein subjected to heating by the aforementioned heating means. The first chamber 25 also has an outlet opening, in a position preferably opposite to that of the inlet opening, from which the steam can exit to leave the reservoir 22.

Figure 3:
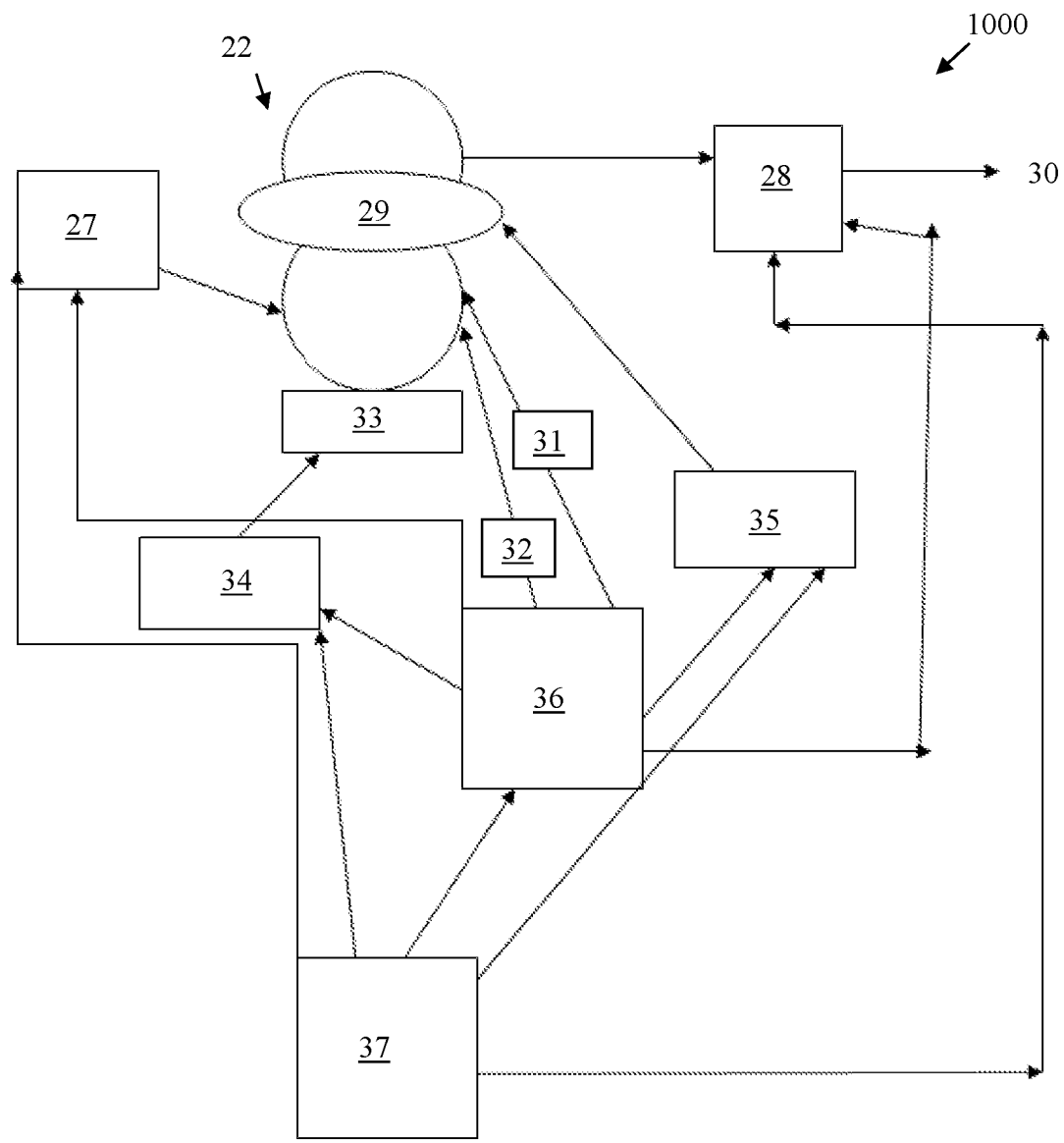
FIG. 3 shows an exemplary block diagram of a third preferred embodiment of a system according to the present invention.

With yet reference to FIG. 3, the system 1000 can further comprise a dispensing valve 28 which determines the quantity, in other words the dosage, of the vaporized substance to be delivered and a turbine pump 27 for conveying air to be supplied at the inlet to the reservoir 22, to realize a flow of conveying the vaporized substance. The air flow can enter the second chamber 26 by means of an inlet 44 (FIG. 4), while the outlet of the air flow and the vaporized substance is denoted by 30.

Such configuration and functionality of the reservoir 22 allows the release of the molecular aggregates of the solutions in a very short time, at biologically tolerable temperatures.

Furthermore, the system 1000 preferably comprises a temperature sensor 31 and a pressure sensor 32, as well as a processor 36 for controlling the vaporization and delivery means, and rechargeable batteries 37 which supply power to the sensors and to the vaporization means and conveying the substance vaporized/to be vaporized.

In particular, the reservoir 22 can be made of aluminium. Preferably, the first and the second chamber have a cylindrical conformation, even more preferably concentric. According to this embodiment, the diameter of the second chamber can measure about from 5 to 7 cm, preferably 6 cm (depending on the amount of solution to be vaporized), while the height of the reservoir 22, measured according to a direction orthogonal to the bottom wall 39, can measure about from 5 to 7 cm, preferably 6 cm.

Hereinafter, a preferred embodiment of a substance containing an active ingredient bound to a solvent by means of the system 1 according to the present invention is described.

The substance is inserted in the reservoir 2, comprised in the vaporizer group 50. The vaporizer group 50 is connected to the support body 100. Depending on the type of substance to be delivered and on the expected administration therapy, the user selects a predetermined delivery program by means of interface means 8, or performs a manual adjustment of the delivery parameters. Alternatively, the control unit 7 automatically adopts a predetermined delivery program, stored in a memory unit 9. Depending on the predetermined delivery program or the manual adjustment performed, the control unit 7 commands the implementation of the first vaporization means 3 and/or second vaporization means 4, independently from each other. The activation of such first 3 and second 4 vaporization means can be carried out in succession, or in simultaneous mode.

When the first vaporization means 3 is activated, this applies to the substance a mechanical vibratory energy in association with an energy density such that realizes the break of the molecular bonds in the substance, both between the active ingredient and the solvent, and between the molecules of the active ingredient same.

When the second vaporization means 4 is activated, this applies to the substance a thermal energy such that realizes the break of the molecular bonds both between the active ingredient and the solvent, and between the molecules of the active ingredient itself.

When the first and second vaporization means 3, 4 are implemented simultaneously, the frequency of the vibrations, the energy density and the heat transferred to the substance are appropriately regulated by the control unit 7, in such a way as to break the molecular bonds and bring the substance into the physical state of dry saturated steam.

Once the substance has been vaporized, the control unit 7 controls the actuation of the pickup means 5, which brings the substance vaporized from the reservoir 2 to the dispensing means 6, applying a predetermined pressure. Eventually, the substance is expelled through dispensing means 6, which operates a regulation of the speed and direction of the steam delivered. Furthermore, the dosage of the solution delivered by means of a block valve is realized at the dispensing means 6.

Following, preferred operating parameters of the system according to the present invention, which can be implemented by means of each of the embodiments described above, are reported.

With reference to solutions of drugs not particularly sensitive to heat, it is possible to activate only the vibratory means to obtain the vaporization of about 5-10 cc of solution, starting from the room temperature (20-25° C.), during less than (about) 1 minute. The operating parameters of the system are listed below: ultrasonic frequency vibration generator in ceramic material operating at a frequency of 5 MHz, powered at 60 W and supplying an energy density of 12 W/cm$^2$.

According to a different mode of vaporization, it is possible to activate the ultrasonic frequency vibratory means and the heating means simultaneously, according to the following operating parameters: ultrasonic frequency vibration generator in ceramic material operating at a frequency of 5 MHz, with power density produced equal to 12 W/cm$^2$, and induction heating by means of a 20 KHz power supply with 60 W of overall power. According to this method, the vaporization of 10 cc of solution is obtained in a time shorter than the second (typically 0.7 sec), with a vaporized substance having particles with a diameter of less than 1 micron and having a temperature between 40° C. and 37° C.

In particular, the vaporization by high frequency ultrasounds (5 MHZ) and high energy density (10-12 $W/cm^2$, much higher than the vaporization threshold which is typically 2.5 $W/cm^2$) assisted by the transfer of thermal energy (from 20° C. to 40°/45° C. to the patient) produces particles with a diameter of less than a micron in a time less than 1 second. Therefore, considering the latency time (6/10 seconds) before the re-condensation, the particles are able to reach the pulmonary alveoli and the blood flow.

The present invention has been so far described with reference to preferred embodiments. It is to be understood that there may be other embodiments which refer to the same inventive core, as defined by the scope of protection of the claims set forth below.

The invention claimed is:

1. A system for delivery of a liquid substance in a form of saturated dry steam for a respiratory therapy through a nasal and/or oral device, comprising:

a support body;

a reservoir for containing the substance;

pickup devices, removably connectable to said reservoir;

dispensing devices of the liquid substance, said dispensing devices being in fluid communication with said pickup devices, said dispensing devices having a passage section for the liquid substance, presenting an area and a geometry configured to allow the delivery of the liquid substance according to predetermined direction and speed parameters;

first mechanical vaporization devices of vibrating type, configured to apply vibrations to the liquid substance contained in the reservoir;

second heating vaporization devices, configured to release thermal energy to the liquid substance contained in said reservoir;

a control unit configured to control an actuation of said first mechanical vaporization devices and said second heating vaporization devices according to a predetermined delivery program, wherein said predetermined delivery program defines at least a frequency and duration values of the vibrations applied by said first mechanical vaporization devices and temperature values and duration of heating operated by said second heating vaporization devices, said predetermined delivery program being associated with a type of therapy and a type of the liquid substance to be delivered, wherein said first mechanical vaporization devices and said second heating vaporization devices are configured to be activated jointly depending on an automatic or manual selection, wherein said reservoir, said dispensing devices, said first mechanical vaporization devices, and said second heating vaporization devices are configured to be removably connected to said support body in such a way as to create a modular system, wherein said first mechanical vaporization devices are configured to apply to the liquid substance vibrations at an ultrasonic frequency, and wherein said second heating vaporization devices comprise induction devices supplied with current at a frequency between 15 and 25 KHz and configured to bring the temperature of the substance to at least 250° C. in such a way as to bring the liquid substance contained in said reservoir into a saturated dry steam state.

2. The system according to claim 1, having a configuration such as to achieve vaporization of the liquid substance into the saturated dry steam state in a time shorter than 1 second.

3. The system according to claim 1, wherein said predetermined delivery program provides simultaneous activation of said first mechanical vaporization devices and said second heating vaporization devices in such a way as to bring the substance into the saturated dry steam state.

4. The system according to claim 1, wherein said first mechanical vaporization devices and said second heating vaporization devices are integral with said reservoir, in such a way as to be selectively removable from said support body together with said reservoir.

5. The system according to claim 1, further comprising interface devices connected to said control unit and configured to allow a user to select the predetermined delivery program.

6. The system according to claim 1, wherein said first mechanical vaporization devices comprise a vibrating element made of ceramic material.

7. The system according to claim 1, wherein said second heating vaporization devices are means applied at least at a bottom portion of said reservoir.

8. The system according to claim 1, wherein said dispensing devices are selectively interchangeable.

9. The system according to claim 1, wherein said dispensing devices comprise a block valve connected to said control unit, which can be actuated to stop the dispensing according to a predetermined dosage.

10. The system according to claim 1, wherein said pickup devices of the substance from said reservoir comprises a pump and a non-return valve.

11. The system according to claim 1, wherein the reservoir comprises a first chamber and a second chamber reciprocally in fluid communication in such a way that a saturated dry steam can flow from said second chamber to said first chamber, wherein said second chamber is configured in such a way as to at least partially circumscribe said first chamber, wherein said first mechanical vaporization devices are connected to said second chamber and said second heating vaporization devices are connected to said first chamber, said first mechanical vaporization devices being configured in such a way as to apply vibrations to the liquid substance contained in said second chamber to bring it into the saturated dry steam state and said second heating vaporization devices being configured in such a way as to heat the saturated dry steam.

12. The system according to claim 1, comprising:
a further reservoir for containment of a further substance,
a compressor and
connection devices configured to realize a fluid communication between said further reservoir and said compressor, wherein said further reservoir and said compressor are removably connectable to said support body, said compressor is removably connectable to said control unit and said further reservoir is removably connectable to said pickup devices, the configuration of said system being such as to allow nebulization and delivery of the further substance contained in said further reservoir by an actuation of said compressor by said control unit, according to a predetermined delivery program.

* * * * *